(12) United States Patent
Thramann et al.

(10) Patent No.: US 7,959,676 B2
(45) Date of Patent: Jun. 14, 2011

(54) METHOD AND APPARATUS FOR INTERVERTEBRAL DISC SUPPORT AND REPAIR

(75) Inventors: Jeff Thramann, Longmont, CO (US); Michael Fulton, Broomfield, CO (US)

(73) Assignee: Lanx, Inc., Broomfield, CO (US)

(*) Notice: Subject to any disclaimer, the term of this patent is extended or adjusted under 35 U.S.C. 154(b) by 357 days.

(21) Appl. No.: 11/354,275

(22) Filed: Feb. 13, 2006

(65) Prior Publication Data

US 2007/0213825 A1    Sep. 13, 2007

(51) Int. Cl.
A61F 2/44    (2006.01)

(52) U.S. Cl. .......................... 623/17.11; 606/76

(58) Field of Classification Search ............... 606/61; 623/17.11–17.16

See application file for complete search history.

(56) References Cited

U.S. PATENT DOCUMENTS

| | | | |
|---|---|---|---|
| 3,867,728 A * | 2/1975 | Stubstad et al. ........... 623/17.16 |
| 5,755,797 A * | 5/1998 | Baumgartner ............. 623/17.16 |
| 6,224,630 B1 * | 5/2001 | Bao et al. .................... 623/17.16 |
| 6,500,190 B2 | 12/2002 | Greene, Jr. et al. |
| 6,511,492 B1 | 1/2003 | Rosenbluth et al. |
| 6,537,569 B2 | 3/2003 | Cruise |
| 6,602,261 B2 * | 8/2003 | Greene et al. ............... 606/108 |
| 6,605,101 B1 | 8/2003 | Schafer et al. |
| 6,607,538 B1 | 8/2003 | Ferrera et al. |
| 6,685,722 B1 | 2/2004 | Rosenbluth et al. |
| 6,689,141 B2 | 2/2004 | Ferrera et al. |
| 6,786,876 B2 | 9/2004 | Cox |
| 6,805,695 B2 * | 10/2004 | Keith et al. ................. 623/17.11 |
| 6,878,384 B2 | 4/2005 | Cruise et al. |
| 7,223,227 B2 * | 5/2007 | Pflueger ......................... 600/12 |
| 2002/0176880 A1 | 11/2002 | Cruise et al. |
| 2003/0014075 A1 | 1/2003 | Rosenbluth et al. |
| 2003/0023190 A1 | 1/2003 | Cox |
| 2003/0195630 A1 * | 10/2003 | Ferree .......................... 623/17.16 |
| 2003/0220695 A1 * | 11/2003 | Sevrain ....................... 623/17.16 |
| 2004/0133232 A1 | 7/2004 | Rosenbluth et al. |
| 2004/0193246 A1 | 9/2004 | Ferrera |
| 2005/0004560 A1 | 1/2005 | Cox |
| 2005/0004660 A1 | 1/2005 | Rosenbluth et al. |
| 2005/0149108 A1 | 7/2005 | Cox |
| 2005/0171572 A1 | 8/2005 | Martinez |
| 2005/0196426 A1 | 9/2005 | Cruise et al. |
| 2006/0287729 A1 * | 12/2006 | Segal et al. ................. 623/17.16 |
| 2007/0150059 A1 * | 6/2007 | Ruberte et al. ............. 623/17.12 |

OTHER PUBLICATIONS

Microvision Awarded Key Patent for Smart Hydrogel, May 11, 2005 (1 page).

* cited by examiner

*Primary Examiner* — Eduardo C Robert
*Assistant Examiner* — Andrew Yang
(74) *Attorney, Agent, or Firm* — Holland & Hart LLP

(57) ABSTRACT

An intervertebral disc device is provided to support or repair one or both of the disc annulus and the disc nucleus. The intervertebral disc device includes an annulus support and an elongated member to support the disc nucleus. The disc annulus support has an elongated wire and an annulus closure. The disc nucleus has an elongated member that is expandable. Any of the devices can be loaded with biologics. Moreover, any of the devices may include a scarring factor to promote fibrous growth.

12 Claims, 5 Drawing Sheets

US 7,959,676 B2

METHOD AND APPARATUS FOR INTERVERTEBRAL DISC SUPPORT AND REPAIR

FIELD OF THE INVENTION

The present invention relates to intervertebral discs and, more particularly, to devices to provide nucleus and annulus support and repair.

BACKGROUND OF THE INVENTION

Many people experience back pain. Back pain, however, is a symptom that can occur from a number of different causes, such as, for example, arthritic facets, degenerating discs, pinched nerves, or the like. Determining the source of the back pain is often one of the challenges in treating the symptom.

Some back pain is caused by degeneration or other deformity of the intervertebral disc ("diseased disc"). Conventionally, surgeons treat diseased discs by surgically removing the diseased disc and inserting an implant in the space vacated by the diseased disc, which implant may be bone or other biocompatible implants. The adjacent vertebrae are then immobilized relative to one another. Eventually, the adjacent vertebrae grow into one solid piece of bone.

Removing the disc and fusing the vertebrae together generally relieves the back pain. However, the fused segments decrease movement and limits the range of motion of the spine. Moreover, fusing the segments together places additional stress on adjacent vertebral segments. The increased stress may increase or initiate degeneration of the adjacent vertebral segments. Thus, for less severe diseased discs, the conventional treatment of fusion maybe an overly aggressive or traumatic solution.

Less severe diseased discs still subject the person to some back pain. Typically, the back pain can be associated with inflammation or instability of the disc. Inflammation can arise from numerous factors, including, for example, the proteins in the disc space or disc nucleus. Instability can also arise from numerous factors, including, for example, when the disc annulus wears down, is damaged, or is compromised (through a hole, tear, or the like), the ability of the disc annulus to resist movement results in instability and may cause pain. Dehydration of the disc also can cause back pain or the like.

In these less severe cases, the treatment may include surgical alternatives. Surgical alternatives include diet, weight control, exercise, stretching, medication, and the like. While helpful, the surgical alternatives frequently only delay the degenerative process and may only partially relieve pain. Thus, it would be desirous to provide other methods and apparatuses to repair, support, or otherwise treat the intervertebral disc.

SUMMARY OF THE INVENTION

The present invention provides an intervertebral disc device. The device comprises an annulus support having an exterior surface to contact a disc annulus and define an interior volume surrounding a disc nucleus and a disc nucleus support residing in the interior volume. The disc nucleus support comprises an elongated wire and at least one expandable material affixed to the elongated wire, wherein the expandable material is expandable in the disc nucleus.

The present invention also provides for a disc annulus device comprising an elongated, flexible material substantially sized to conform to an interior surface of a disc annulus. The disc annulus device also comprises a disc annulus closure device coupled to the elongated, flexible material to close an insertion point in the disc annulus.

The present invention also provides for a disc nucleus device comprising an elongated, flexible wire. At least one expandable material affixed to the elongated, flexible wire for insertion into a disc nucleus, whereby the expandable material expands and provides support between a superior vertebrae and an inferior vertebrae.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
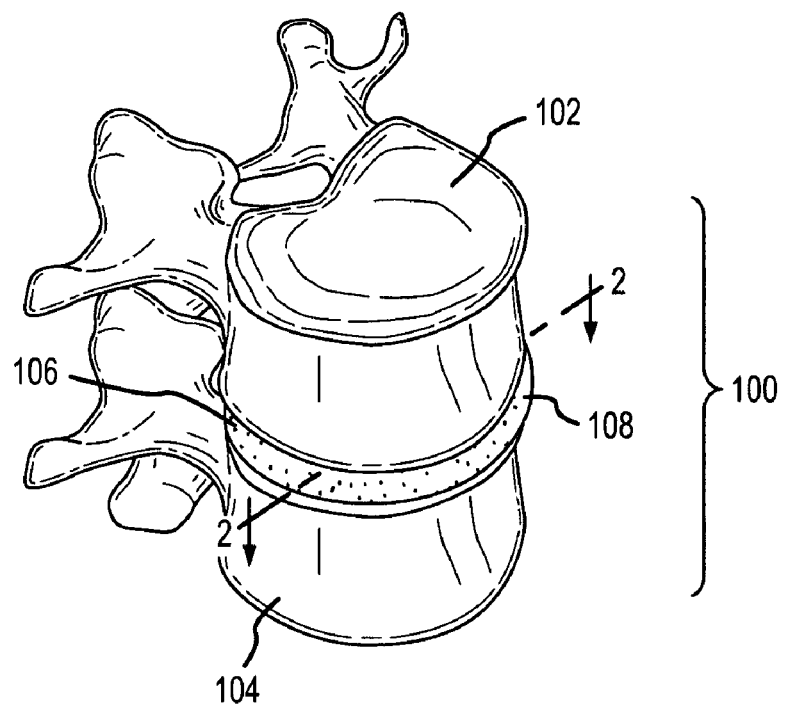
FIG. 1 is a perspective view of a vertebral segment.
Figure 2:
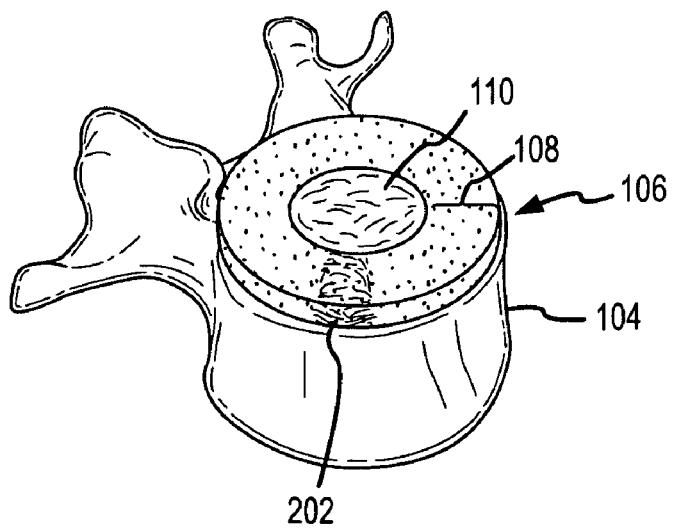
FIG. 2 is a cross sectional view of the vertebral segment of figure one showing the disc annulus.

The present invention will be described with reference to the figures. Referring first to FIG. 1, a vertebral segment. 100 is shown. Vertebral segment 100 includes a superior vertebral body 102 and an inferior vertebral body 104 separated by an intervertebral disc 106. Intervertebral disc 106 comprises a disc annulus 108' containing a disc nucleus 110 (which is best seen in FIG. 2). Referring now to FIG. 2, a cross sectional view of intervertebral disc 106 is shown. Disc 106 includes disc annulus 108 and disc nucleus 110. Disc 106 is shown with some degeneration 202 in disc annulus 108. Degeneration 202 could be any number of anatomical conditions, such as, for example, a tear, a bulge, inflammation, or the like.

Conventional treatments to decrease or remove pain caused by degeneration 202 include, medications, therapy, and the like. Medications, therapy, and the like, while beneficial for a significant number of people, do not ease the pain for everyone. Many people require additional surgical treatment to ease the pain. The conventional treatment, as mentioned above, is fusing superior vertebral body 102 and inferior vertebral body 104 producing a single bone segment without any intervertebral disc 106. This treatment has some significant drawbacks. Other less conventional treatments include cauterizing the natural disc annulus, replacement of the intervertebral disc with an artificial disc, replacing the disc nucleus with a hydrogel, and the like. Each of these procedures, while addressing some of the drawbacks associated with fusion, have drawbacks as well. For example, artificial discs have significant failure rates. Cauterizing the disc annulus reduces the flexibility of the disc. Hydrogels may cause bulging about the annulus or become displaced from the disc space. Other drawbacks also exist.

Figure 3:
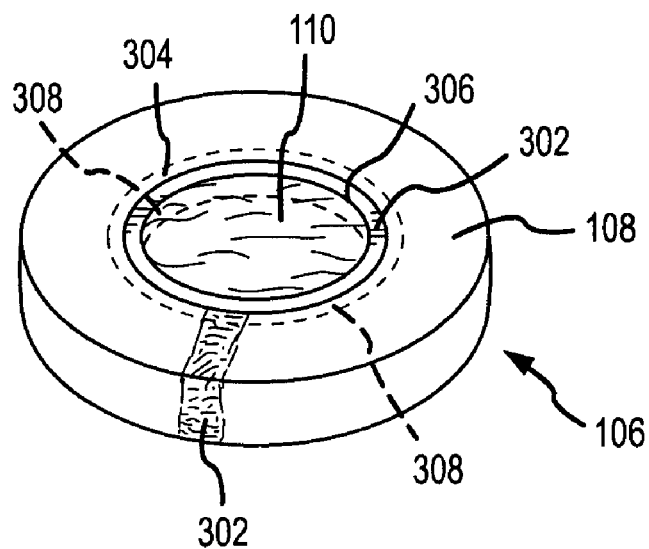
FIG. 3 is a perspective view of the disc annulus with an annulus support.

Referring now to FIG. 3, a perspective view of disc 106 with annulus support 302 is shown. Disc annulus 108 includes degeneration 202. Also shown in FIG. 3, is an annulus support 302. Annulus support 302 as shown is a loop of material internal to disc 106. Disc nucleus 110 (not specifically shown in FIG. 3) tends to push annulus support 302 against disc annulus 1.08. Annulus support 302 provides structural stability to disc annulus as well as cover degeneration 202, which inhibits further degradation of disc 106. Optionally, a scarring material 304, such as, for example, cotton or the like may reside between annulus support 302 and disc annulus 108 to promote fibrous growth, which would facilitate disc repair. Scarring material 304 could be arranged about the entire annulus support 302 as shown or localized to the area with degradation 202.

Annulus support 302 may be sized to extend from superior vertebral body 102 to inferior vertebral body 104 as shown. Alternatively, annulus support 302 may be sized to correspond to degeneration 202. Still alternatively, annulus support 302 may be a relatively small wire to deliver scarring material 304 to degeneration 202. Scarring material 304 promotes fibrous growth to repair disc annulus 108.

Figure 4:
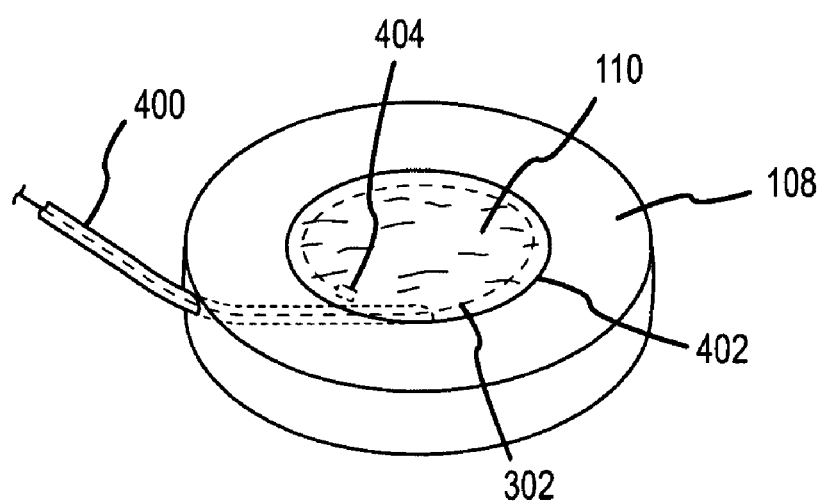
FIG. 4 shows the implantation of the annulus support of FIG. 3.

Referring now to FIG. 4, a method of delivering annulus support 302 is shown. A delivery mechanism 400 is inserted through disc annulus 108 into disc nucleus 110. Delivery mechanism 400 may be a needle, a dilator, a catheter, or the like. Annulus support 302 is threaded through delivery mechanism 400. Annulus support 302 is threaded into disc nucleus 110 until it bumps or contacts an interior surface 402 of disc annulus 108. Annulus support 302 is further threaded where annulus support 302 bends along the interior surface 402 until it completely travels interior surface 402. Annulus support 302 is either fully threaded at this point, detached by any conventional detachment device, or cut and packed into disc nucleus 110. Delivery mechanism 400 is: removed. To the extent a scarring material 304 is not otherwise provided, a tip 404 of annulus support 302 may be provided with a scarring material 304 such that when fully wrapped about interior surface 402, scarring material 304 is generally aligned with the insertion point of delivery mechanism 400 to promote fibrous growth and healing of the insertion point.

As one of ordinary skill in the art will now appreciate on reading the above, annulus support 302 should provide sufficient structural support to facilitate disc 106 functionality, but be sufficiently resilient to be directed by disc annulus 108 during insertion. One such material could be a shaped memory alloy ("SMA"), such as, for example, NiTiol. SMAs provide acceptable materials because they have both elastic and inelastic phases. Other polymers, resins, metals, alloys, and the like also could be used. To facilitate wrapping, tip 404 may be beveled or shaped to help guide annulus support 302 around interior surface 402. Generally, to facilitate implantation, support 302 should be an expandable material. However, non-expandable materials are acceptable, but will require additional surgical trauma.

Figure 5:
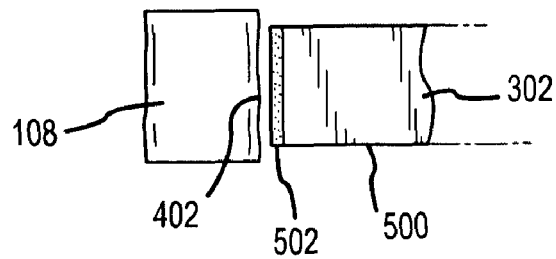
FIG. 5 shows a tail of one annulus support.
Figure 6A:
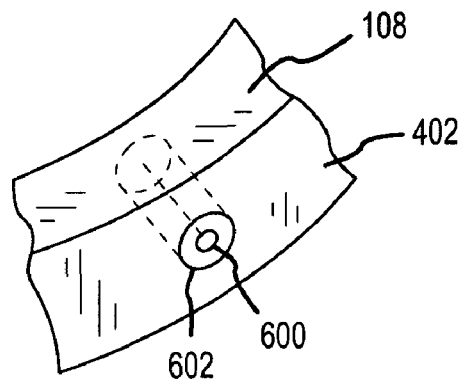
FIG. 6a shows an annulus closure mechanism prior to expansion.
Figure 6B:
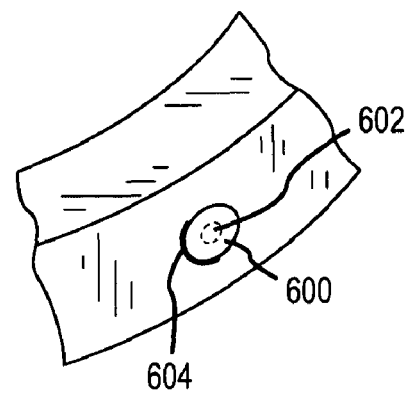
FIG. 6b shows an annulus closure mechanism post expansion.

Referring to FIG. 5, a tail 500 of annulus support 302 is shown adjacent interior surface 402 of disc annulus 108. Tail 500 is shown in a compact insertion format 500c instead of an expanded format as shown by 302. Tail 500 may include scarring material 502 such that material 502 is aligned with the insertion point of delivery mechanism 400. Scarring material 502 on tail 500 can be used in conjunction with or in the alternative to scarring material 304 on tip 404. The insertion point may be covered by a separate closure device 600, shown in FIGS. 6a and 6b. As shown in FIG. 6a, closure device 600 is inserted in a collapsed or compressed package, 600c about insertion point 602 in disc annulus 108. As shown in 6b, closure device 600 has expanded 600e to be larger than insertion point 602 covering the insertion. Closure device 600 may be held about insertion point 602 by annulus support 302 or by an adhesive 604, which could comprise a scarring material 304 to promote fibrous growth. Closure device 600 could be a stand alone device, connectable or integrated with annulus support 302.

Referring back to FIG. 3, annulus support 302 provides support for disc annulus 108 and could also deliver biologic or pharmaceuticals (generally referred to as either biologics or pharmaceuticals) to either disc annulus 108 or disc nucleus 110. For example, inner surface 306 of annulus support 302 could be loaded with biologics 308 designed to assist in re-growth or repair of disc nucleus material 110. Moreover, biologics 308 could be contained on outer surface 308 or loaded in scarring material 304 if used. Types of biologics that could be delivered include, for example, FGF-beta, BMP-12, OP-1, TGF-betal, cultured autologous annular fibrosis or nuclear pulposes cells or other biologics that aid the repair of the annulus or the nucleus, or the like.

Figure 7:
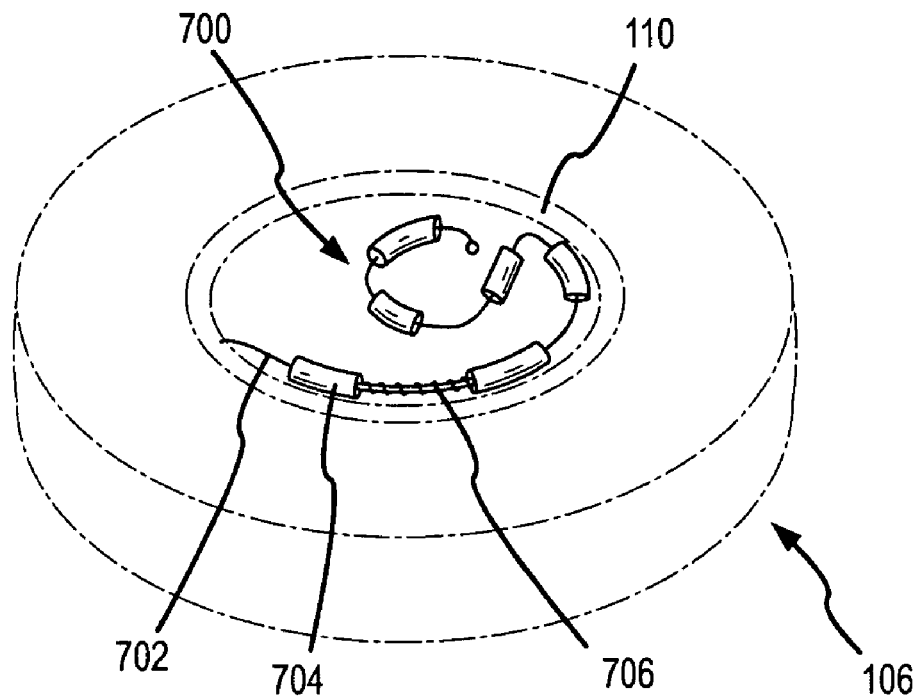
FIG. 7 shows a nucleus support.

Referring now to FIG. 7, disc 106 (shown in phantom) is shown with a disc nucleus support 700. Disc nucleus support 700 could be used to augment or replace the biological disc nucleus 110. Moreover, disc nucleus support 700 could be used separately or in conjunction with an annulus support. Disc nucleus support 700 includes a wire 702 carrying several capsules 704 of expandable material. The number of capsules 704 will depend, in part, on the size of the disc space as well as whether the entire disc nucleus is being replaced or whether the disc nucleus is being augmented. Spacers 706 (of which only one is shown for convenience), such as coils wrapped about wire 702, may be placed between capsules to maintain separation for proper expansion of the capsules.

Wire 702 may be any biocompatible wire. Wire 702 could be constructed from titanium, platinum, SMAs, plastics, composites, resins, polymers, or the like. Capsules 704 can be any biocompatible expandable material. For example, capsules 704 could be hydrophilic foam or gel material that swells. One such material is described in U.S. Pat. No. 5,570,585, issued to Park et al., the disclosure of which is incorporated herein by reference as if set out in full. Other suitable materials are described in U.S. Pat. No. 6,602,261, issued to Creene, Jr. et al., the disclosure of which is incorporated herein by reference as if set out in full. Other suitable, materials include polymers, resins, composites, SMAs, spring metals, and other expandable biocompatible materials. Ideally, the amount, of expansion is controllable and/or predictable so a sufficient number of capsules 704 can be implanted into disc nucleus 110 to provide sufficient support to alleviate pain. For, example capsules 704 may be as described in U.S. Pat. No. 6,878,384, issued to Curise et al., which is incorporated herein by reference as if set out in full, described materials that swell or expand in a predictable manner.

Figure 8A:
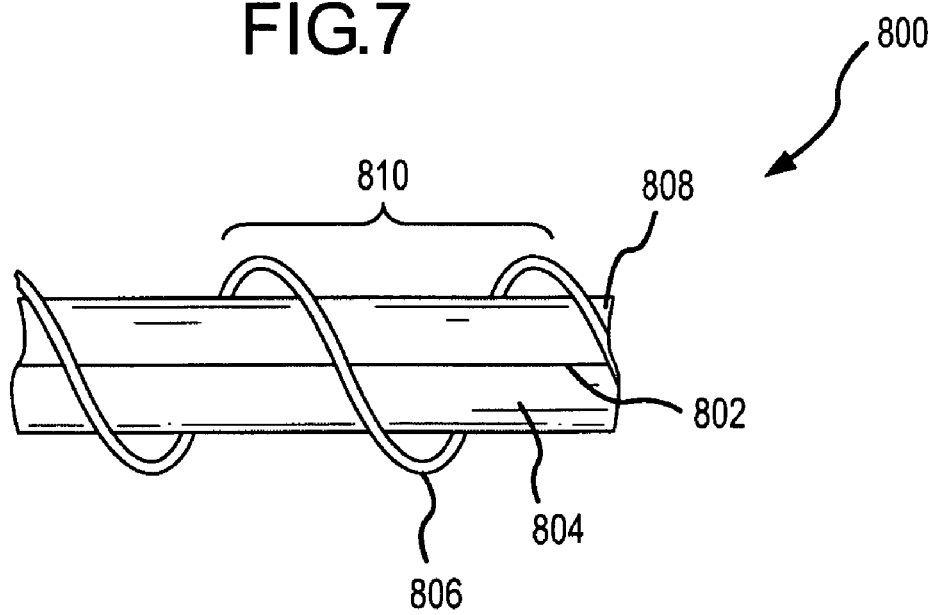
FIGS. 8a and 8b shows another nucleus support.
Figure 8B:
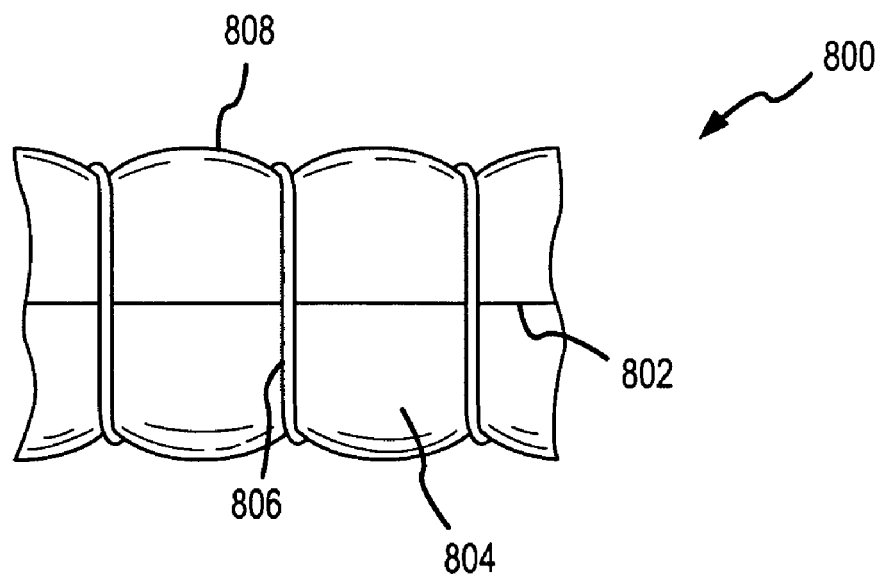

Referring now to FIG. 8a, another nucleus support 800 is provided. Nucleus support 800 provides a wire 802 or filament. Expandable material 804 extends over substantially the entire wire 802. Optionally, an over coil 806 for expansion control, expansion direction, trackability, or durability is provided. In the unexpanded state, over coil 806 resides a distance from an outer surface 808 of expandable material 804. Over coil 806 provides a number of gaps 810 to allow limited or directed expansion of expandable material 804. FIG. 8b shows nucleus support 800 in the expanded state and FIG. 8a shows nucleus support 800 in the non-expanded state.

Figure 9:
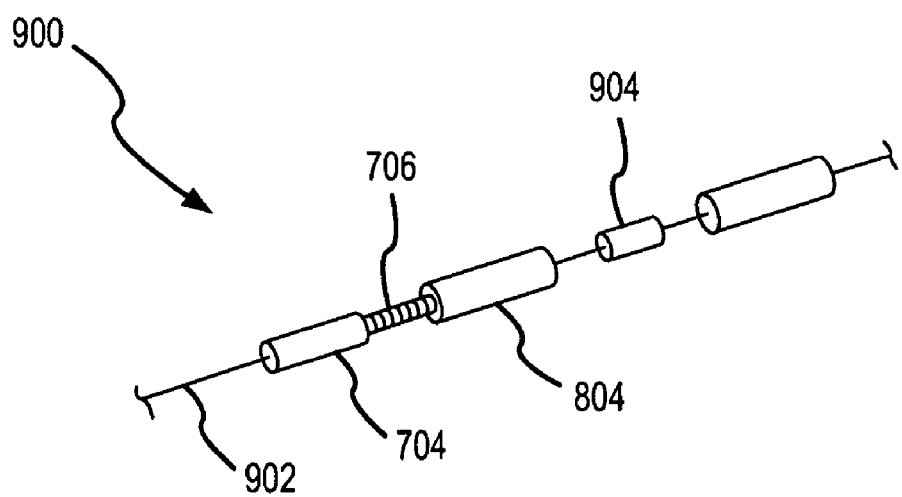
FIG. 9 shows a pharmaceutical delivery device.

Referring now to FIG. 9, a biologics delivery mechanism 900 is provided. Biologics delivery mechanism 900 includes a wire 902 with one or more capsules 904 including biologics or the like, as described above. Biologics delivery mechanism 900 optionally may include capsules 704 or expandable material 804 interspersed with the one or more biologics capsules 904 such that biologics delivery mechanism 900 also functions as a nucleus support mechanism. Optionally, biologics mechanism 900 may have spacers, such as spacers 706 described above, or an expansion control attachment 806.

Devices 700, 800, and 900 could be delivered to the disc nucleus 110 in a manner similar to annulus support 302. The expandable material should sufficiently impinge on the insertion point to sufficient close the insertion point, but a closure mechanism such as closure device 600 could also be used. Closure device 600 may be seated against the disc annulus by the expandable material.

Wires 702, 802, and 902 should be sufficiently elastic to be able to pack into disc nucleus without piercing disc annulus 108. They could be comprised from, for example, SMAs, such as, nitinol, polymers, resins, platinum, titanium, or the like.

While the invention has been particularly shown and described with reference to some embodiment thereof, it will be understood by those skilled in the art that various other changes in the form and details may be made, without departing from the spirit and scope of the invention.

The invention claimed is:

1. A disc nucleus device comprising:
   an elongated, flexible wire, the elongated, flexible wire comprises a tip and a tail;
   an expandable disc annulus closure device coupled to at least one of the tip or the tail; and
   at least one expandable material affixed to the elongated, flexible wire sized for insertion into a disc nucleus, the at least one expandable material extending substantially continuously along the elongated, flexible wire, and an expansion control member disposed around at least a portion of the elongated, flexible wire, wherein the expansion control member is configured to provide expansion control of the at least one expandable material in a radial direction from the elongated, flexible wire, and the expandable material configured to expand in the disc nucleus and to provide support between a superior vertebrae and an inferior vertebrae.

2. The disc nucleus device according to claim 1, further comprising at least one capsule coupled to the elongated, flexible wire, the at least one capsule comprising a pharmaceutical.

3. An intervertebral disc device comprising:
   an annulus support having an exterior surface and an interior volume adapted to surround a disc nucleus;
   a scarring material adapted to reside between the exterior surface and a disc annulus to promote fibrous growth;
   a disc nucleus support residing in the interior volume, and the disc nucleus support comprising an elongated wire, at least one expandable material affixed to the elongated wire, and an over coil disposed in a surrounding configuration to the elongated wire, wherein the over coil is configured to provide expansion control of the at least one expandable material, and wherein the expandable material is expandable in the disc nucleus.

4. The intervertebral disc device according to claim 1, wherein the at least one expandable material comprises a plurality of capsules of expandable material.

5. The intervertebral disc device according to claim 4, wherein at least one of the plurality of capsules of expandable material comprises a hydrogel material.

6. The intervertebral disc device according to claim 1, further comprising a pharmaceutical delivery capsule affixed to the elongated wire.

7. The intervertebral disc device according to claim 1, wherein the annulus support has an interior surface further comprising a carrier, the carrier containing at least one pharmaceutical.

8. The intervertebral disc device according to claim 1, wherein the annulus support has a tip and a tail further comprising scarring material on at least one of the tip or the tail to cause fibrous growth at an insertion point.

9. The annulus device according to claim 1, wherein the elongated wire is selected from a group of materials consisting of: a polymer, a resin, a composite, titanium, platinum, or shaped memory alloys.

10. The annulus device according to claim 1, wherein the scaring material is cotton.

11. The annulus device according to claim 1, wherein the elongated, flexible material is adapted to substantially surrounds a disc nucleus.

12. A device to deliver pharmaceuticals to a disc nucleus, the device comprising:
   a filament, the filament comprising an expandable closure device coupled to an end of the filament;
   at least one capsule coupled to the filament, the at least one capsule containing at least one pharmaceutical;
   the at least one capsule adapted to provide support between a superior vertebrae and an inferior vertebrae; and
   at least one expandable material coupled to the filament to provide support between the superior vertebrae and the inferior vertebrae, and an over coil disposed in a surrounding configuration to the filament and in a surrounding configuration to the at least one capsule coupled to the filament, wherein the over coil is configured to provide expansion control of the at least one expandable material.

* * * * *